US012642448B2

(12) United States Patent
Cheung et al.

(10) Patent No.: US 12,642,448 B2
(45) Date of Patent: Jun. 2, 2026

(54) METHOD AND SYSTEM FOR ASSESSING HUMAN MOVEMENTS

(71) Applicant: Surge Motion Inc., Alhambra, CA (US)

(72) Inventors: Jeffrey Tai Kin Cheung, Fremont, CA (US); Derek T. Cheung, San Mateo, CA (US); Vicky L Cheung, Portland, OR (US); Gary N. Jin, Portland, OR (US)

(73) Assignee: SURGE MOTION INC., Alhambra, CA (US)

( * ) Notice: Subject to any disclaimer, the term of this patent is extended or adjusted under 35 U.S.C. 154(b) by 1222 days.

(21) Appl. No.: 16/588,227

(22) Filed: Sep. 30, 2019

(65) Prior Publication Data

US 2020/0107750 A1     Apr. 9, 2020

Related U.S. Application Data

(60) Provisional application No. 62/740,559, filed on Oct. 3, 2018.

(51) Int. Cl.
*A61B 5/11*          (2006.01)
*A61B 5/06*          (2006.01)
*G06V 40/20*         (2022.01)

(52) U.S. Cl.
CPC ............ *A61B 5/067* (2013.01); *A61B 5/1117* (2013.01); *A61B 5/112* (2013.01); *G06V 40/23* (2022.01)

(58) Field of Classification Search
None
See application file for complete search history.

(56) References Cited

U.S. PATENT DOCUMENTS 4,712,807 A  * 12/1987  Kurosawa ............ B60G 17/016
                                                        280/5.507
7,457,719 B1 * 11/2008  Kahn ................... G01C 22/006
                                                        702/141
(Continued)

FOREIGN PATENT DOCUMENTS

CN       108471987  A  *  8/2018  ............. A61B 5/113
WO       2017216103 A1   12/2017
WO    WO-2020071375 A1 *  4/2020

OTHER PUBLICATIONS

Xingran Cui et al. "Development of a new approach to quantifying stepping stability using ensemble empirical mode decomposition", Science Direct, Gait & Posture, Article Received Feb. 14, 2013, Received in revised form Aug. 28, 2013, Accepted Aug. 30, 2013.

*Primary Examiner* — Aurelie H Tu
(74) *Attorney, Agent, or Firm* — Shun Yao; Yao Legal Services, Inc.

(57)          ABSTRACT

One embodiment provides a system for analyzing a motion. During operation, the system obtains acceleration data associated with the motion. The acceleration data can include three components corresponding to three spatially orthogonal directions. For each orthogonal direction, the system computes an amount of oscillatory energy included in the motion in the orthogonal direction based on a corresponding acceleration component. For at least one orthogonal direction, the system obtains an energy fraction factor by computing a ratio between the amount of the oscillatory energy in the orthogonal direction and a total amount of the oscillator energy. The system generates a motion-analysis output based at least on the energy fraction factor.

12 Claims, 9 Drawing Sheets

(56)  References Cited

U.S. PATENT DOCUMENTS

| | | | | |
|---|---|---|---|---|
| 7,753,861 | B1 * | 7/2010 | Kahn | A61B 5/1118 |
| | | | | 600/595 |
| 10,307,086 | B2 | 6/2019 | Cheung | |
| 10,327,671 | B2 | 6/2019 | Cheung | |
| 2006/0251334 | A1 * | 11/2006 | Oba | A61B 5/1122 |
| | | | | 382/275 |
| 2008/0246734 | A1 * | 10/2008 | Tsui | H02J 7/00302 |
| | | | | 345/169 |
| 2010/0168958 | A1 * | 7/2010 | Baino | B62J 6/027 |
| | | | | 702/94 |
| 2011/0021317 | A1 * | 1/2011 | Lanfermann | A61B 5/1127 |
| | | | | 482/8 |
| 2014/0276119 | A1 * | 9/2014 | Venkatraman | A61B 5/02405 |
| | | | | 600/509 |
| 2016/0192866 | A1 * | 7/2016 | Norstrom | A61B 5/1123 |
| | | | | 434/247 |
| 2017/0042453 | A1 | 2/2017 | Cheung | |
| 2018/0220935 | A1 | 8/2018 | Tadano et al. | |
| 2020/0297243 | A1 * | 9/2020 | Katsuhara | A61B 5/742 |

* cited by examiner

METHOD AND SYSTEM FOR ASSESSING HUMAN MOVEMENTS

RELATED APPLICATION

This application hereby claims priority under 35 U.S.C. § 119 to U.S. Provisional Patent Application No. 62/740,559, filed on 3 Oct. 2018, entitled "Method of Assessing Human Movement," by inventors Jeffery T. Cheung, Derek T. Cheung, Vicky L. Cheung, and Gary N. Jin.

BACKGROUND

Field of the Invention

This disclosure is generally related to analysis of human movements. More specifically, this disclosure is related to a method and system that analyzes movement data to obtain spatial energy distribution associated with the movements.

Related Art

Gait analysis (i.e., the study of walking and running forms) has provided important information to the study of biomechanics. Traditional gait analysis uses an elaborate optoelectronic setup with multiple light-emitting diodes (LEDs) and reflective markers placed on various parts of a subject under test. During test, high-speed cameras are used to capture sequential frames when the subject is moving (e.g., walking or running). Information regarding the movements of the subject can be extracted using a frame-by-frame analysis followed by complex computations. Such approaches are cumbersome, expensive, inefficient, and can only be performed offline (e.g., after the testing is done). The development of various high-precision motions sensors, such as accelerometers and gyroscopes, has made it easier to obtain a vast amount of movement data without the need of the elaborate optoelectronic setup. Motion analysis relying on such sensor data has found applications in many areas.

SUMMARY

One embodiment provides a system for analyzing a motion. During operation, the system obtains acceleration data associated with the motion. The acceleration data can include three components corresponding to three spatially orthogonal directions. For each orthogonal direction, the system computes an amount of oscillatory energy included in the motion in the orthogonal direction based on a corresponding acceleration component. For at least one orthogonal direction, the system obtains an energy fraction factor by computing a ratio between the amount of the oscillatory energy in the orthogonal direction and a total amount of the oscillator energy. The system generates a motion-analysis output based at least on the energy fraction factor.

In a variation on this embodiment, the motion can be substantially along a horizontal plane. The three orthogonal directions can include a medial lateral (ML) direction, a vertical (VT) direction, and an anterior posterior (AP) direction. The system can compute a motion quality factor based on one or more energy fraction factors corresponding to the ML, VT, and AP directions.

In a further variation, the motion quality factor can include one or more of: a stability factor, an efficiency factor, and a symmetry index.

In a variation on this embodiment, computing the amount of the oscillatory energy can include performing a frequency-domain analysis on the acceleration data.

In a further variation, performing the frequency-domain analysis can include: performing a Fourier transform (FT) on the acceleration data to obtain a plurality of frequency components of the acceleration; computing, for each frequency of a predetermined set of frequencies, a frequency component of the oscillatory energy; and summing the computed frequency components of the oscillatory energy.

In a variation on this embodiment, the motion can include a human movement or a movement associated with a machine.

In a variation on this embodiment, obtaining the acceleration data can include attaching a motion sensor substantially near a center of gravity of a subject performing the motion and obtaining outputs from the motion sensor.

In a further variation, the motion sensor can include at least one of: a three-axis accelerometer, a gyroscope, and a magnetometer.

BRIEF DESCRIPTION OF THE FIGURES

In the figures, like reference numerals refer to the same figure elements.

DETAILED DESCRIPTION

Overview

Embodiments of the present invention provide a system and method for performing motion analysis using data collected by a set of high-precision sensors that include at least a tri-axis accelerometer, a gyroscope, and a magnetometer. During operation, the sensors can be mounted on a user's body at a location close to his center of gravity (e.g., at the lower back). Hence, movements (e.g., acceleration) of the center of gravity when the user is walking or running can be measured. Different phases of a movement cycle (e.g., walking or running a step) can be identified based on the measured movement data. Moreover, motion energy included in each phase can be computed and decomposed along the three spatially orthogonal axes. By studying the distribution of energies among the three orthogonal directions, one can obtain important information associated with the health, wellness, physical performance, and/or age of the user.

Gait Analysis Based on Sensor Data

Figure 1:
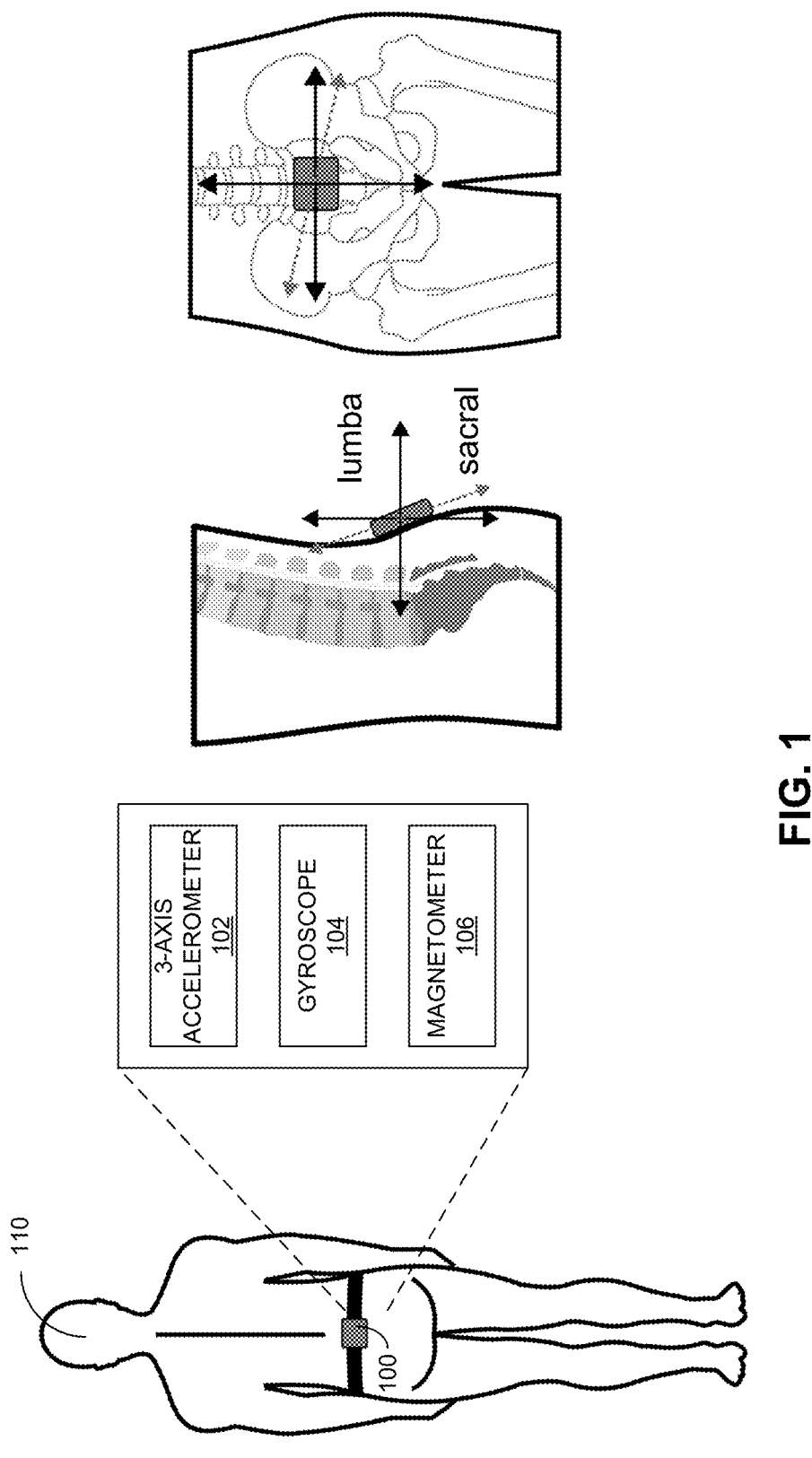
FIG. 1 illustrates a motion sensor mounted on a human body, according to one embodiment.

FIG. 1 illustrates a motion sensor mounted on a human body, according to one embodiment. In FIG. 1, motion sensor 100 can include at least a three-axis accelerometer 102, a gyroscope 104, and a magnetometer 106. Motion sensor 100 can record movements in all six-degrees of freedom, including three translations (surge, sway, and heave) and three rotations (roll, pitch, and yaw). Note that surge refers to the forward-and-backward motion (along the X-axis), sway refers to the left-and-right motion (along the Y-axis), and heave refers to the up-and-down motion (along the Z-axis); whereas roll refers to tilting side-to-side on the X-axis, pitch refers to tilting forward-and-backward on the Y-axis, and yaw refers to turning left-and-right on the Z-axis.

FIG. 1 shows that motion sensor 100 is mounted on the lower back of user 110. More specifically, motion sensor 100 can be placed directly behind the lumbosacral joint of user 110, as shown in more details by the two right drawings of FIG. 1. Various mounting mechanisms can be used to mount motion sensor 100 on user 110, including but not limited to: attaching to a belt, clipping onto an item of clothing, taping directly onto the body, etc. It is not necessary that motion sensor 100 maintains an upward orientation; the system can detect and compensate for the tilt of motion sensor 100.

During measurement, user 110 can perform a required movement (e.g., walking, running, swimming, pedaling a bike) for a predetermined duration and outputs of the various modules in motion sensor 100 can be recorded. The sampling rate of motion sensor 100 can be between a few hertz and a few thousand hertz, as long as the sampling rate is sufficiently high to capture changes of the movement. A motion that changes rapidly (e.g., a high speed rotation) will require motion sensor 100 to have a higher sampling rate. In some embodiments, the sampling rate can be roughly 100 Hz. The sensor data can be processed in real time. In alternative embodiments, the sensor data can be processed offline.

Figure 2:
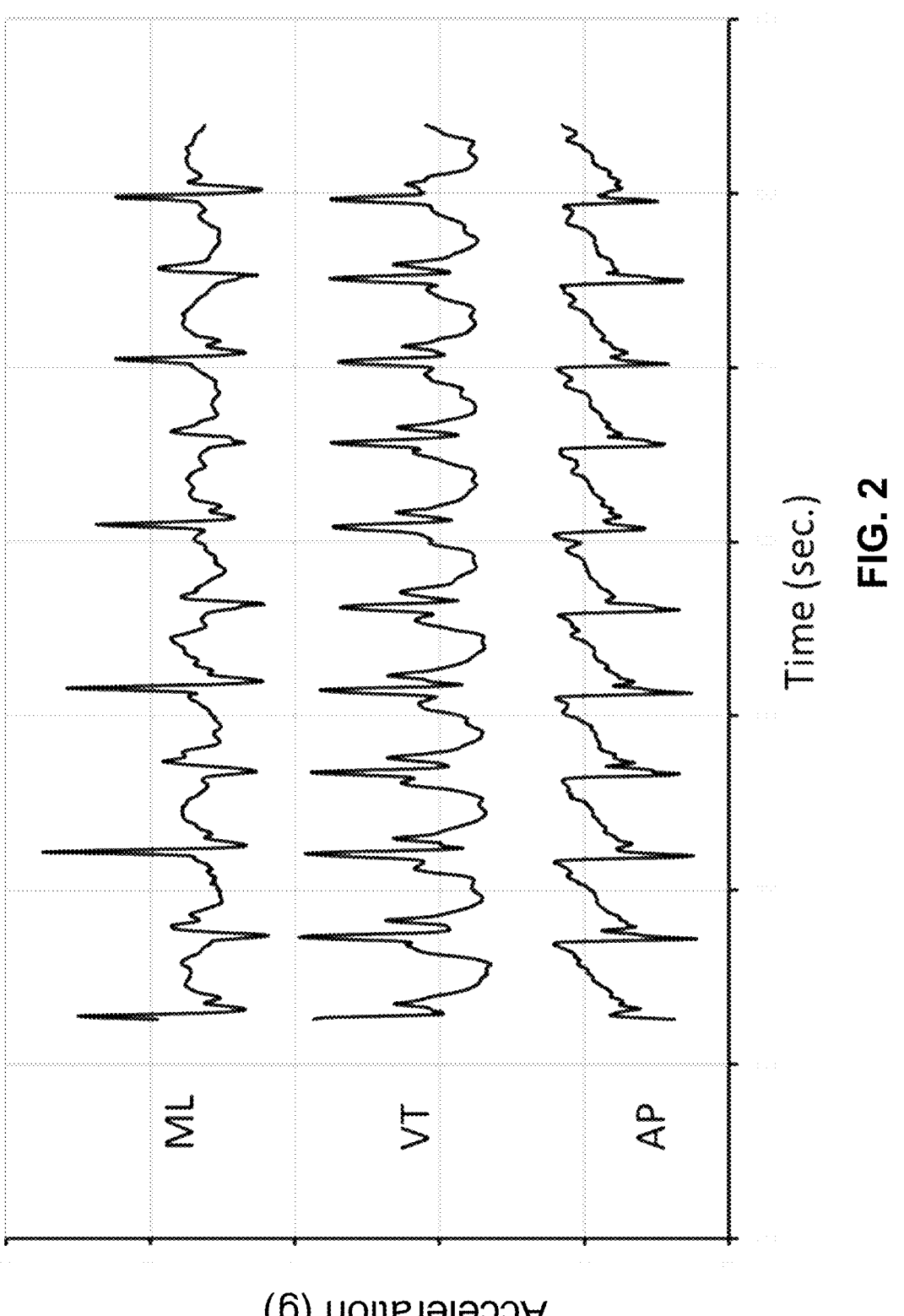
FIG. 2 illustrates exemplary sensor data, according to one embodiment.

Raw sensor data can include time-dependent acceleration data along with rotational gyro data, which can be separately processed. FIG. 2 illustrates exemplary sensor data, according to one embodiment. The acceleration data can be obtained along the three orthogonal directions: Medial Lateral (or sway) $A(t)_{ML}$, Vertical (or heave) $A(t)_{VT}$, and Anterior Posterior (or surge) $A(t)_{AP}$. Various types of information associated with the movement of the user can be extracted from the sensor data. For example, the major peaks in the acceleration data correspond to the fundamental frequency (e.g., stride frequency) of the motion. Therefore, by observing the peaks, one can determine the stride frequency and/or the stride length. Moreover, one can plot the three-dimensional (3D) trajectory of the acceleration vector, which is unique to each individual and can provide important biomechanical information regarding the user's movements.

However, conventional approaches for gait or motion analysis are mostly concerned with the displacement, velocity, and acceleration of the user's center of gravity and often ignore the kinetic energy involved in the movements. In contrast, embodiments of the present invention perform an energy analysis by calculating the distribution of the kinetic energy in different phases of a movement cycle among different orthogonal directions. Information extracted from this energy analysis can be used to measure the quality of the movement and to infer the health condition of the user.

For a human movement that is oscillatory in nature (e.g., running, cycling, and swimming) and is traversing a leveled or slightly graded surface, the amount of energy included in the motion can include two portions: the non-oscillatory motion energy and the oscillatory motion energy. The non-oscillatory motion energy is used to move the subject forward (e.g., the kinetic energy included in the forward motion). The amount of non-oscillatory motion energy can be calculated as $$E = \frac{1}{2}mV_{ave}^2,$$

where m is the mass of the subject (i.e., the person) and $V_{ave}$ is the average velocity. On the other hand, the oscillatory energy is used to maintain balance and/or control a body part (e.g., lift up a foot) during the movement, and can be much smaller than the non-oscillatory motion energy. Using walking as an example, the amplitude of the oscillatory motion (e.g., the sway and the bouncing up and down of the body) can be about 10 times smaller than the stride length (e.g., 5 cm vs. 50 cm). As a result, the oscillatory motion energy can be 100 times smaller than the non-oscillatory motion energy. However, despite such a large disparity in magnitude, the oscillatory motion energy can provide vital information associated with the movement. For example, the partition of the oscillatory motion energy along the three orthogonal axes can be used to gauge gait quality and assess fall risk. In addition to human movements, various types of machine movement (e.g., the running of a car and the rotating of a wind turbine) may also be cyclic in nature and motion energy associated with such movements can also be partitioned into the non-oscillator motion energy and the oscillatory motion energy.

To calculate the oscillatory motion energy from the raw acceleration data, one can first transform the acceleration data from the time domain to the frequency domain (e.g., by performing a Fourier transformation) to obtain:

$$A(t)_{ML}=a_{ML1}e^{i\omega_{ML1}t}+a_{ML2}e^{i\omega_{ML2}t}+a_{M3}e^{i\omega_{ML3}t}+ \ldots,$$

$$A(t)_{VT}=a_{VT1}e^{i\omega_{VT1}t}+a_{VT2}e^{i\omega_{VT2}t}+a_{VT3}e^{i\omega_{VT3}t}+ \ldots,$$

and $$A(t)_{AP}=a_{AP1}e^{i\omega_{AP1}t}+a_{AP2}e^{i\omega_{AP2}t}+a_{AP3}e^{i\omega_{AP3}t}+ \ldots,$$

where $a_i$ is the amplitude for each frequency (e.g., $\omega_i$) component.

The displacement X(t) can be computed by integrating the acceleration function twice: $X(t)=\iint A(t)dt$. Therefore, for each frequency component, the displacement is $$X_i(t) = -\frac{a_i}{\omega_i^2}e^{i\omega_i t}.$$

The oscillatory motion energy in the three orthogonal axes can be computed based on the displacement vectors. In some embodiments, the oscillatory energy can be computed using the following expressions:

$$E_{ML} = \frac{m}{8\pi^2}\left[\left(\frac{a_{ML1}}{f_{ML1}}\right)^2 + \left(\frac{a_{ML2}}{f_{ML2}}\right)^2 + \left(\frac{a_{ML3}}{f_{ML3}}\right)^2 + \ldots\right],$$

-continued $$E_{VT} = \frac{m}{8\pi^2}\left[\left(\frac{a_{VT1}}{f_{V1}}\right)^2 + \left(\frac{a_{VT2}}{f_{V2}}\right)^2 + \left(\frac{a_{VT3}}{f_{V3}}\right)^2 + ...\right], \text{ and}$$

$$E_{AP} = \frac{m}{8\pi^2}\left[\left(\frac{a_{AP1}}{f_{AP1}}\right)^2 + \left(\frac{a_{AP2}}{f_{AP2}}\right)^2 + \left(\frac{a_{AP3}}{f_{AP3}}\right)^2 + ...\right].$$

Note that $E_{ML}$ is the amount of energy included in side-to-side motion, $E_{VT}$ is the amount of energy included in the up-and-down motion, and $E_{AP}$ is the amount of energy included in the back-and-forth motion. The total amount of the oscillation motion energy (e.g., the amount of energy consumed by the user during walking but does not contribute to the forward motion) can be calculated as $E_{Total}=E_{ML}+E_{VT}+E_{AP}$.

As one can imagine, an efficient and healthy gait should include a lesser amount of energy in the sway and surge directions. Hence, by computing the amount of motion energy in the sway and/or surge directions and by comparing such energy amount to the total amount of oscillatory motion energy, one can determine the effectiveness or correctness of a person's gait. In some embodiments, the fraction of the oscillatory motion energy included in the sway (ML) direction can be denoted $EF_{ML}$, where $EF_{ML}=E_{ML}/E_{Total}$. Similarly, the energy fractions in the heave (VT) and surge (AP) directions can be expressed as: $EF_{VT}=E_{VT}/E_{Total}$ and $EF_{AP}=E_{AP}/E_{Total}$, respectively.

Figure 3:
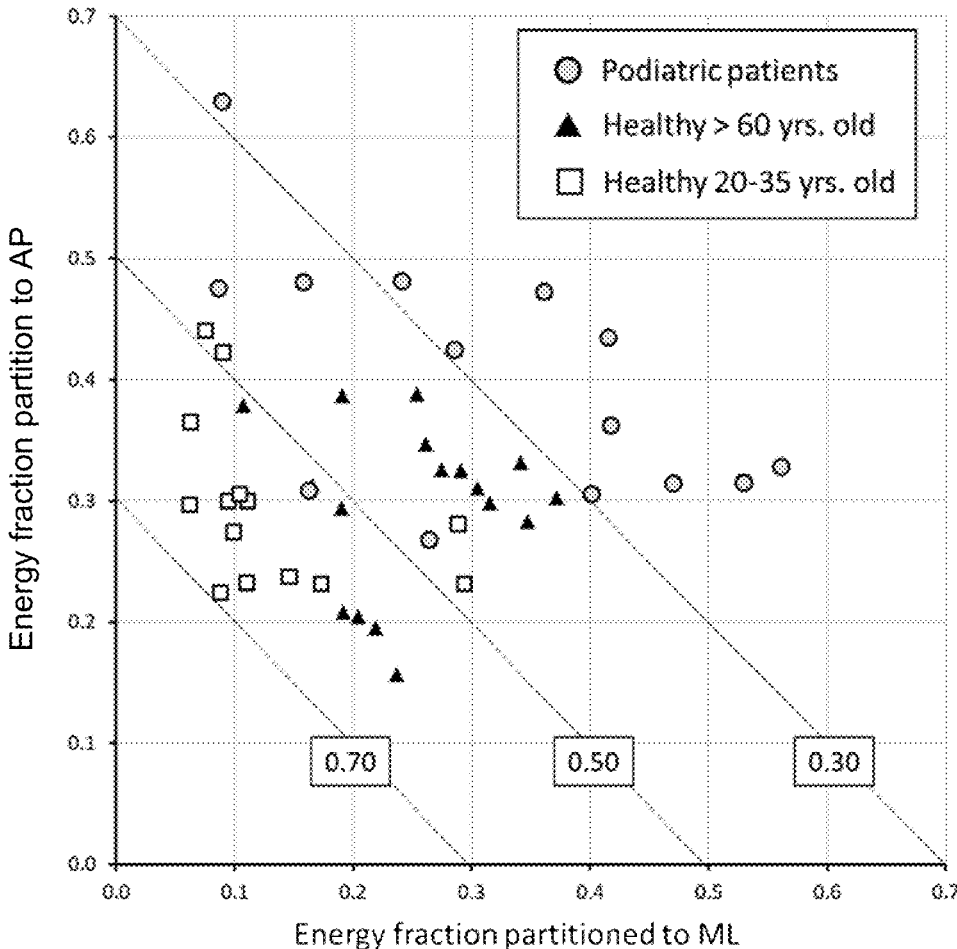
FIG. 3 plots the energy fraction in the AP direction against the energy fraction in the ML direction for gaits of a group of individuals of different ages and health, according to one embodiment.

FIG. 3 plots the energy fraction in the AP direction against the energy fraction in the ML direction for gaits of a group of individuals of different ages and health, according to one embodiment. More specifically, the raw acceleration data is obtained when the individuals are walking on a flat surface. One can see from FIG. 3 the clustering of the data points for different groups of individuals. The data points for younger and healthy individuals (as shown by the squares) are clustered to the left and lower portion of the graph, indicating that the fractions of energy used by the AP and ML motions are relatively small. In fact, the majority of the data points for these individuals are between a straight line connecting (0, 0.3) and (0.3, 0) and a straight line connecting (0, 0.5) and (0.5, 0), indicating that the total fraction of the oscillator energy in the horizontal plane is between 30% and 50%.

On the other hand, the data points for older and healthy individuals (as shown by the triangles) are shifting upwardly and to the right in the graph. The total energy fractions included in the horizontal plane for these individuals are typically between 50% and 70%. The rest of the data points belong to podiatric patients (as shown by the circles). These patients tend to have a larger fraction of the total oscillatory energy (e.g., more than 70%) being consumed in the horizontal plane while walking. In other words, patients with foot problems tend to wobble (i.e., sway or surge) more while walking. Hence, by extracting the energy fraction information from the motion sensor data of a user, one can infer information regarding the health, wellness, performance, and/or age of the user.

Figure 4A:
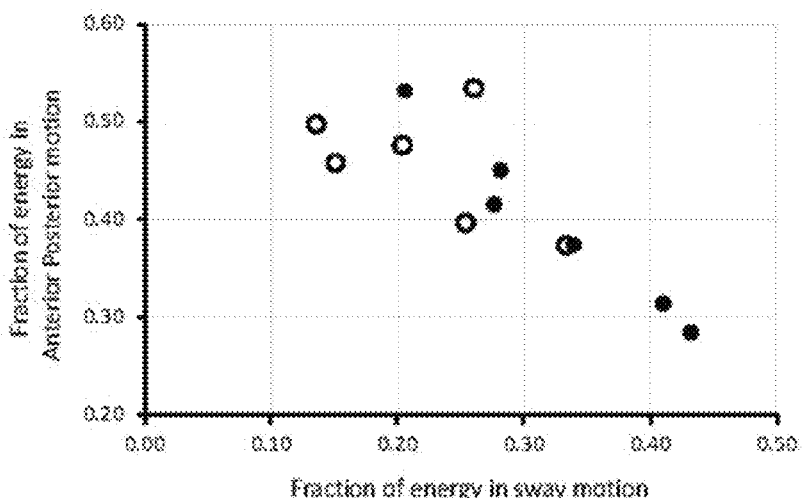
FIG. 4A plots the energy fraction in the AP direction against the energy fraction in the ML direction for gaits under different footwear conditions, according to one embodiment.

In addition to age and/or health, the similar energy fraction information (e.g., the percentage of oscillatory energy included in a particular direction) can also be used to measure or determine the quality of footwear and/or orthotics, and other motion-assisting systems (e.g. skates, skis, fins, etc.). FIG. 4A plots the energy fraction in the AP direction against the energy fraction in the ML direction for gaits under different footwear conditions, according to one embodiment. More specifically, the open circles are data points for gaits wearing sneakers with padding and ankle support and the solid circles are data points for gaits wearing heavy socks. As one can see, the gaits wearing sneakers use a smaller fraction of the oscillatory energy in the ML (or sway) direction, meaning that the sneakers can provide a higher level of stability. While the energy fraction in the ML direction indicates a level of stability, the energy fraction in the AP direction can be a measure of gait efficiency. A smaller energy fraction in the AP direction can indicate a more efficient gait.

Figure 4B:
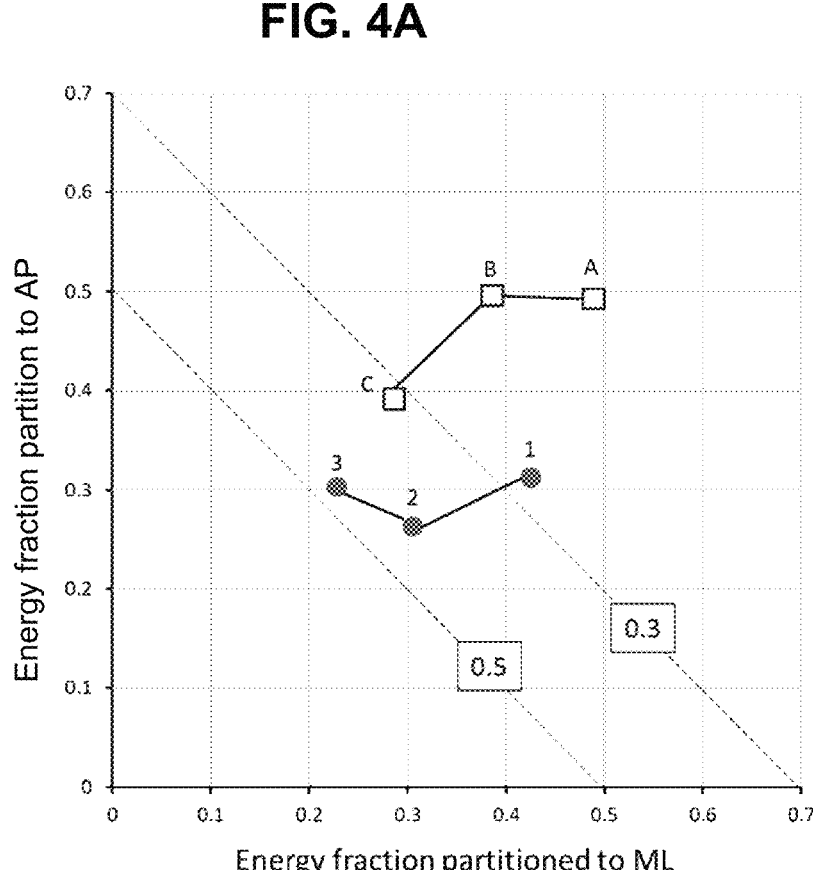
FIG. 4B illustrates the effect of footwear on gait qualities, according to one embodiment.

Similarly, FIG. 4B also illustrates the effect of footwear on gait qualities, according to one embodiment. In FIG. 4B, points A, B, and C are energy analysis results of a particular individual having gait impairments. Point A represents the individual walking barefoot, point B represents the individual wearing shoes with a heel lift, and point C is for the individual wearing shoes with a heel lift and a custom-made insole. Points 1, 2, and 3 are gait analysis result for a different individual with normal gait. This individual walks barefoot (point 1), wears a pair of normal shoes (point 2), and wears a pair of specially designed shoes with a cured sole (point 3). As one can see from FIG. 4B, wearing supportive footwear (especially the custom-designed ones) can improve the test subjects' gait quality by reducing the amount of oscillatory energy being consumed in the horizontal plane. In other words, a larger portion of the oscillatory motion energy is consumed in the VT (up and down) direction. Note that the energy partition in the VT direction can be an indicator of the ground clearance of the gait. A higher VT energy fraction can indicate a larger ground clearance of the gaits. Note that insufficient ground clearance can increase the risk for falling. A person with weak or stiff ankles, knees, and hips often fails to have sufficient ground clearance when walking, thus resulting in gaits exhibiting a smaller energy partition in the VT direction. Therefore, by evaluating the energy partition in the VT direction of a person's gaits, one can estimate or predict the fall risk of that person.

Figure 5:
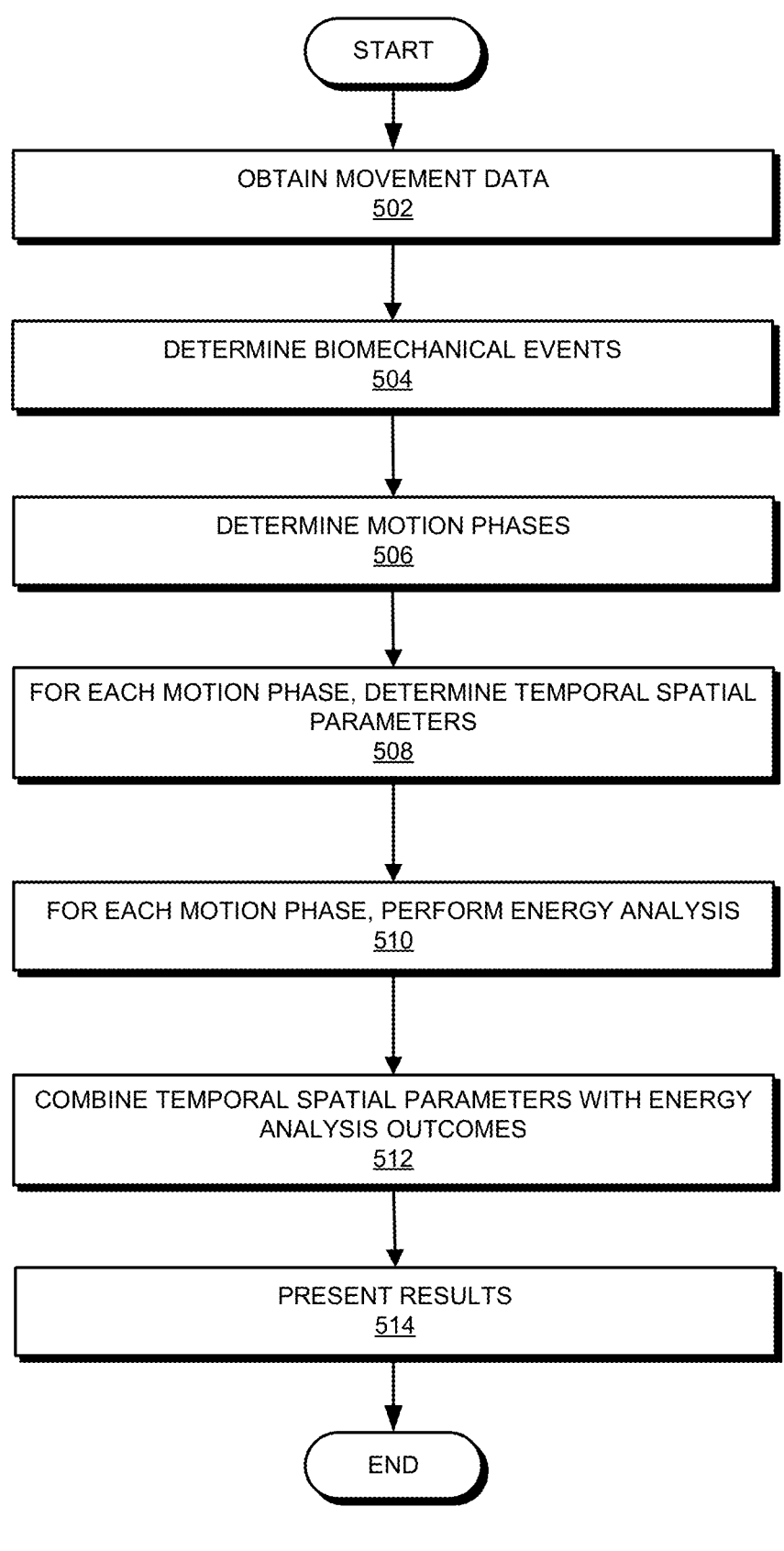
FIG. 5 presents a flowchart illustrating an exemplary motion-analysis process, according to one embodiment.

FIG. 5 presents a flowchart illustrating an exemplary motion-analysis process, according to one embodiment. During operation, the system obtains movement data (e.g., acceleration data) from a motion sensor (operation 502). The motion sensor can include a number of measurement modules capable of measuring different aspects of the movement. The measurement modules can include but are not limited to: a 3-axis accelerometer, a gyroscope, and a magnetometer. Note that, although the 3-axis accelerometer can provide orientation information associated with the movement, the inclusion of a magnetometer can further improve the accuracy of such orientation information. Note that accurate measurement of the orientation of the acceleration is very important in the current application, because it is essential in ensuring the accuracy of the partition of the oscillatory energy into the three orthogonal directions. In some embodiments, the movement data can include sensor data over a predetermined duration. For example, a user may be asked to walk on a flat surface while wearing the sensor and sensor data for a predetermined duration (e.g., 30 seconds) can be extracted and analyzed. The sensor data can be analyzed in real time or offline. The sampling rate of the sensor can be between a few hertz to a few thousand hertz, as long as the sensor sampling rate is sufficiently high for the particular motion being monitored. In some embodiments, the sampling rate of the sensor can be about 100 Hz.

The system can then determine a plurality of biomechanical events or key events from the measured data (operation 504). Using human walking as an example, the biomechanical events can include but are not limited to: heel strike, toe lift, turning, etc. Based on the determined biomechanical events, the system can determine the various phases of the human motion (operation 506). For example, the different phases of a walking gait can include the stance phase, the single-support phase, and double-support phase. The various detected key events can be used to mark the beginning and ending of the different phases of a motion and to determine the duration of each phase.

The system can then determine, for each phase of the motion, various temporal spatial parameters associated with the motion (operation 508). For example, various parameters associated with the human walking motion can include but are not limited to: the stride length, the speed, the ground contact time, etc. Such temporal spatial parameters can be extracted from the raw acceleration data using various known algorithms. The system can also perform, for each phase of the motion, energy analysis (operation 510). In some embodiments, performing the energy analysis can involve computing and partitioning the oscillatory energy associated with the motion along the three orthogonal spatial axes (i.e., ML, VP, and AP directions). More specifically, the system can calculate an energy fraction factor for each orthogonal direction. Various methods can be used to perform the energy analysis. In some embodiments, a frequency-domain analysis (e.g., a Fourier transform (FT) such as a fast FT (FFT)) method is used to compute the oscillatory energy of a motion in each direction.

Figure 6:
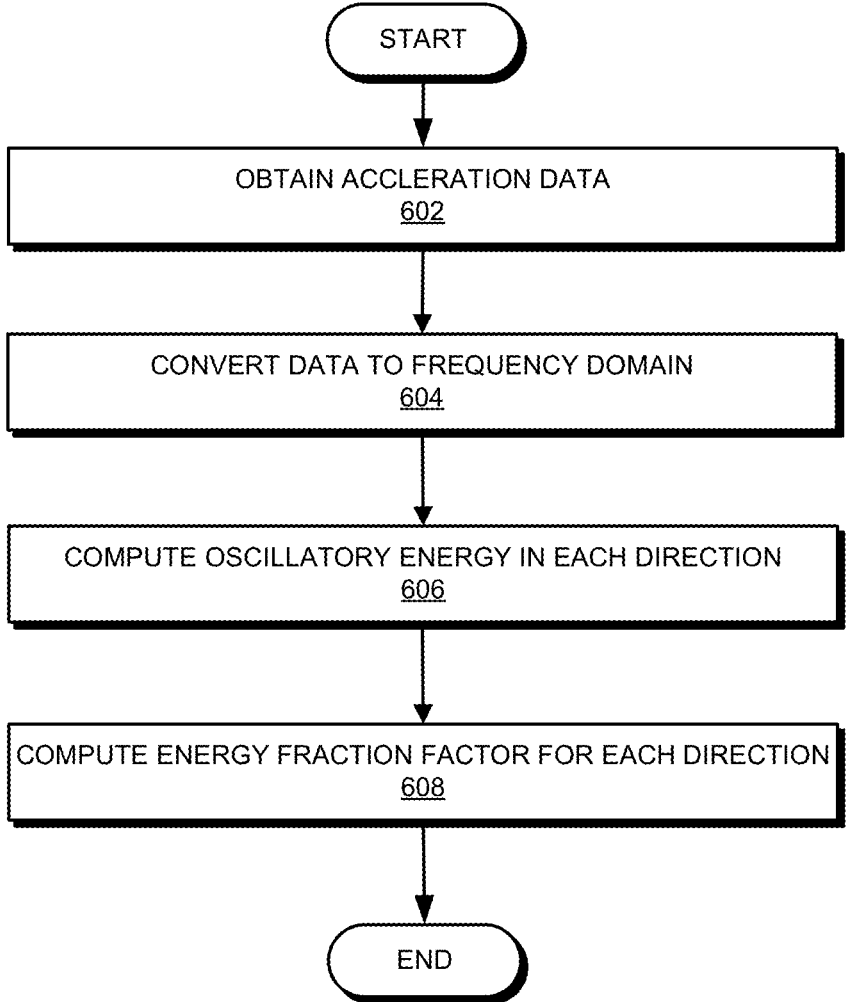
FIG. 6 presents a flowchart illustrating an exemplary energy-analysis process, according to one embodiment.

FIG. 6 presents a flowchart illustrating an exemplary energy-analysis process, according to one embodiment. During operation, the system obtains steady state acceleration data in each orthogonal direction (operation 602). The steady state acceleration data can be obtained from the sensor output. More specifically, certain filtering can be applied to remove sensor noise. Moreover, the fundamental frequency of the motion (e.g., the stride frequency) can also be removed in order to remove the non-oscillatory component.

Subsequently, the system converts the time-domain accelerate data to frequency domain (operation 604). For example, the system can select a number of time-domain data points and performs fast Fourier transform (FFT) on the selected time-domain data points. FFT usually requires $2^n$ (e.g., 512 or 1024) data points. The FFT operation can be performed for each direction, including the ML, VT, and AP directions. The system then computes the amount of oscillatory energy in each direction (operation 606). Note that the oscillatory energy can be computed as a summation of all frequency components. However, because the amplitude for each frequency component is proportional to $1/f^2$, the contribution from the higher frequency components can be negligible. In some embodiments, when computing the oscillatory energy involved in the motion, the system sums up the frequency components up to a predetermined frequency (e.g., 10 or 20 Hz). This can reduce the computation complexity without significantly sacrificing accuracy. The system can further compute the energy fraction factor for each direction (operation 608). In other words, the system can determine the partition of the oscillatory energy among the three spatial components (e.g., the percentage of oscillatory energy partitioned into each of the ML, VT, and AP directions). In some embodiments, for human motions performed on a horizontal plane (e.g., walking or running on a flat surface), the system can further compute a summation of the oscillatory energy fractions of the ML and AP directions. Such a summation can be used as an indicator of motion stability. A higher percentage value often indicates a less stable motion, whereas a lower percentage value can indicate a more stable motion. Motion stability, on the other hand, can be an indicator of optimization and efficiency (e.g., a more stable motion is a motion having a higher degree of optimization and efficiency). For example, the system can define a stability factor as the inverse of the summation of the oscillatory energy fractions of the ML and AP directions. The minimum stability factor can be 1, meaning all oscillatory energy is in the horizontal plane. For a stable gait, the stability factor can be greater than 2, meaning that less than 50% of the oscillatory energy is in the horizontal plane. In alternative embodiments, the stability factor can also be computed as an inverse of the ML energy fraction alone. Computing the stability factor allows the system to evaluate the stability associated with the motion of the subject being tested. In addition to the stability factor, one may use other criteria to describe stability. For example, a stability index on a scale from 0 to 100 can also be defined, where a stability index of 100 can indicate that 100% of the oscillatory energy is distributed in the VT direction. In addition to a stability factor or index, other parameters, such as a symmetry index, a rhythm, and a level of efficiency can also be derived from the energy analysis. All these parameters can be used to measure the quality of a motion and can sometimes be referred to as motion quality factors.

Returning to FIG. 5, the system can subsequently combine the temporal spatial parameters with the outcomes of the energy analysis to obtain a comprehensive description of the human motion (operation 512). Depending on the application, such a comprehensive motion description can be used to obtain various results or conclusions that can be presented to the user. For example, the system can compare each aspect of the motion within the same measurement for the same individual. In other words, the system can show the individual how his gait may vary during the measurement period. For example, based on the temporal spatial analysis, the system can identify from the gait measurement the single support phases of a walking motion. Accordingly, the system can compute the amount of oscillatory energy being consumed in each single support phase, which can provide information regarding the user's risk of falling. In another example, the system can compare the amount of oscillatory energy consumed when the user is turning around to the amount of oscillatory energy consumed when the user is walking on a straight line. The system can also compare each aspect of the motion to results obtained based on past measurement of the same individual. This way, the system can show the individual how his gait changes over time or under different conditions. Moreover, the system can compare each aspect of the motion to results obtained based on measurements of other individuals, to known reference values, or to population distribution results. These comparison results can be used to assess the health, performance, wellness, fitness, and other quality and state associated with the human motions. The system can then present the results to the user (operation 514). In some embodiments, the system can present the results on a user interface of a mobile computing device (e.g., a smartphone or a tablet computer). In one embodiment, the motion sensor can also be integrated into the same mobile device or the system can use the built-in sensors of the mobile device to obtain the measurement data, and the description of the various aspects (e.g., impact forces, symmetry, and energy partitions or decompositions) of the motion. In an alternative embodiment, the motion sensor can be a standalone sensor and the sensor output can be sent to a mobile device for processing. Moreover, the mobile device may also forward the sensor output to a remote server, which processes the sensor output and then sends the motion analysis result back to the mobile device for presentation.

Figure 7A:
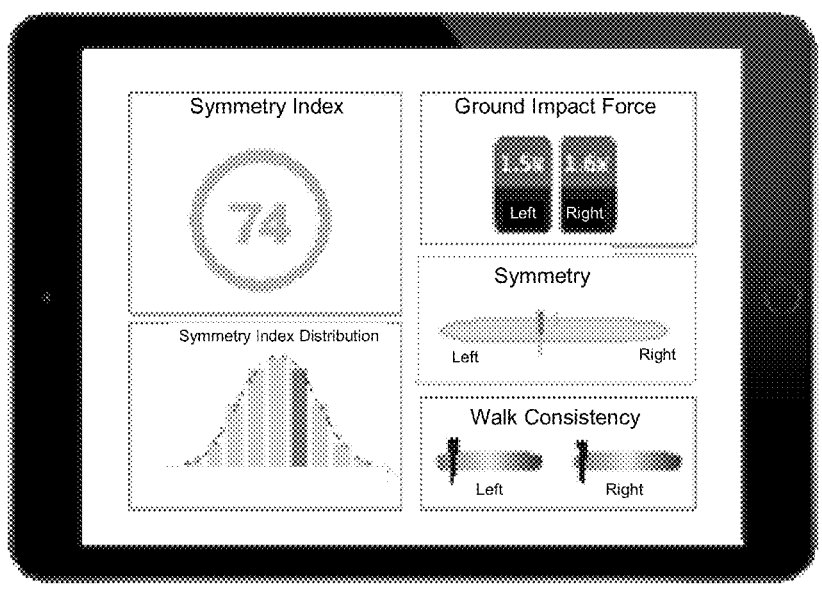
FIG. 7A illustrates an exemplary motion-analysis user interface, according to one embodiment.
Figure 7B:
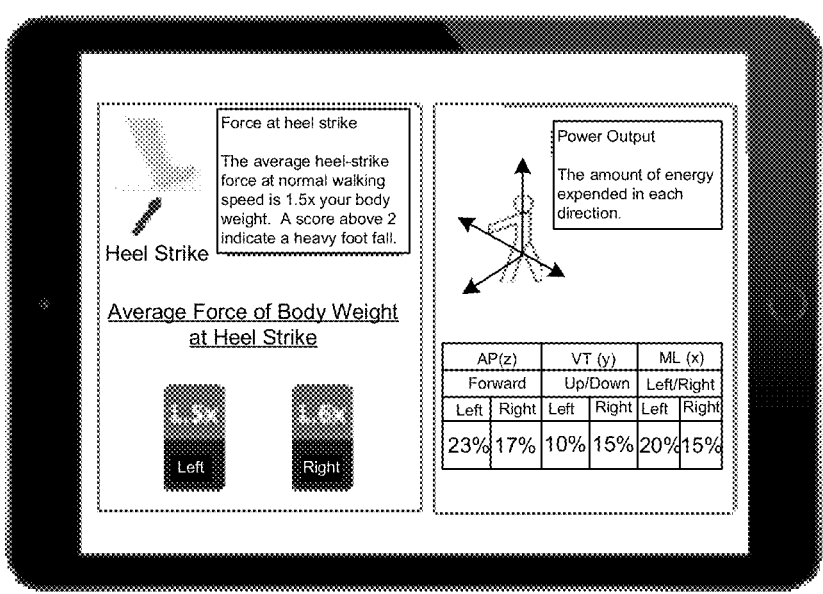
FIG. 7B illustrates another exemplary motion-analysis user interface, according to one embodiment.

FIG. 7A illustrates an exemplary motion-analysis user interface, according to one embodiment. More specifically, FIG. 7A illustrates various outputs of the motion-analysis system. In this example, the subject under test is wearing a motion sensor on his lower back and is walking normally in a straight line for at least 30 seconds. The motion analysis can be performed while he is walking or afterwards. In FIG. 7A, various motion-analysis results regarding the symmetry of the body while walking is given, including a symmetry index and graphics representations of the body motion symmetry. FIG. 7A also shows the ground impact force on each foot. FIG. 7B illustrates another exemplary motion-analysis user interface, according to one embodiment. More specifically, FIG. 7B illustrates the partition of the oscillatory energy along the three orthogonal axes.

In the examples shown in FIGS. 7A and 7B, the motion analysis is performed on gait measurement data. In practice, similar techniques can be used to analyze different types of human motion, including but not limited to: walking, running, swimming, cycling, swinging a golf club, skiing, snowboarding, etc. In general, by discovering the partitioning of the oscillatory energy of a motion among the orthogonal axes, the system is capable of providing information that can be used to measure the stability and/or quality of the motion, thus being a valuable diagnosis tool. In addition to human movements, the similar approach can also be used to assess or diagnose other types of movement, such as movements of an animal (e.g., a horse) and movements of a machine (e.g., automobile, plane, boat, etc.).

Figure 8:
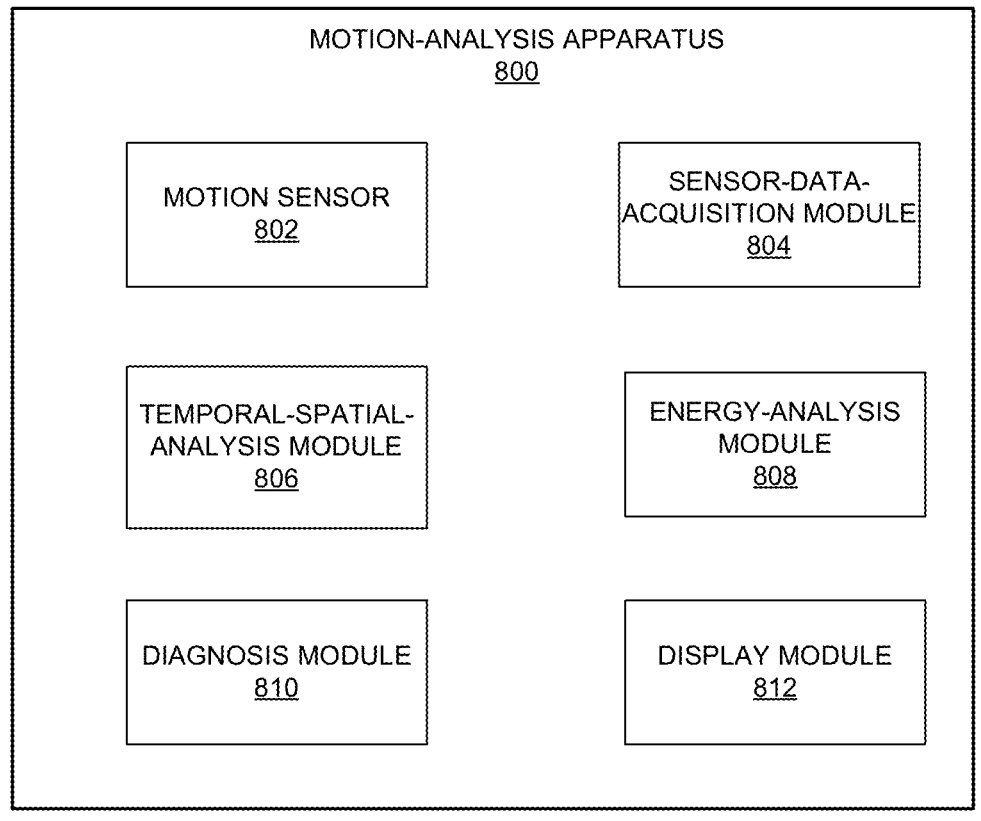
FIG. 8 illustrates an exemplary motion-analysis apparatus, according to one embodiment.

FIG. 8 illustrates an exemplary motion-analysis apparatus, according to one embodiment. Motion-analysis apparatus 800 can include a motion sensor 802, a sensor-data-acquisition module 804, a temporal-spatial-analysis module 806, an energy-analysis module 808, a diagnosis module 810, and a display module 812.

Motion sensor 802 can include one or more measurement modules, including but not limited to: a 3-axis accelerometer, a gyroscope, and a magnetometer. Sensor-data-acquisition module 804 can obtain motion-measurement data from motion sensor 802. In some embodiments, sensor-data-acquisition module 804 can acquire the motion-measurement data via a wireless link (e.g., WiFi™ or Bluetooth™). Alternatively, sensor-data-acquisition module 804 can acquire the motion-measurement data via a wired link (e.g., peripheral component interconnect express (PCIe) or I²C).

Temporal-spatial-analysis module 806 can be responsible for performing motion analysis in the time domain. More specifically, temporal-spatial-analysis module 806 can calculate various temporal spatial parameters, such as speed, time, distance, angle, rotation, etc., from the motion-measurement data.

Energy-analysis module 808 can be responsible for performing energy analysis of the motion based on the motion-measurement data. More specifically, based on the acceleration data, energy-analysis module 808 can compute the amount of oscillatory energy included in the motion. To do that, the non-oscillatory energy component needs to be removed or filtered from the total motion energy. Moreover, the oscillatory motion can be decomposed into three spatially orthogonal directions (the ML, VT, and AP directions), and the oscillatory energy in each direction can be separately computed. Once the oscillatory energy in each direction is known, energy-analysis module 808 can also compute the energy partitions or the energy fraction factors. The energy fraction factor for each direction represents a percentage that the total oscillatory energy is partitioned into that direction. For motions moving along a horizontal plane, the system can further calculate a stability factor, which can be the inverse of the sum of the ML and AP energy fraction factors or the inverse of the ML energy fraction factor.

Diagnosis module 810 can be responsible for generating a number of diagnosis results based on outputs of temporal-spatial-analysis module 806 and energy-analysis module 808. Depending on the application, various types of parameters that can provide insights regarding the quality and efficiency of the motion (e.g., stability, efficiency, and symmetry) can be generated. Display module 812 can be responsible for displaying the diagnosis results to the user.

Figure 9:
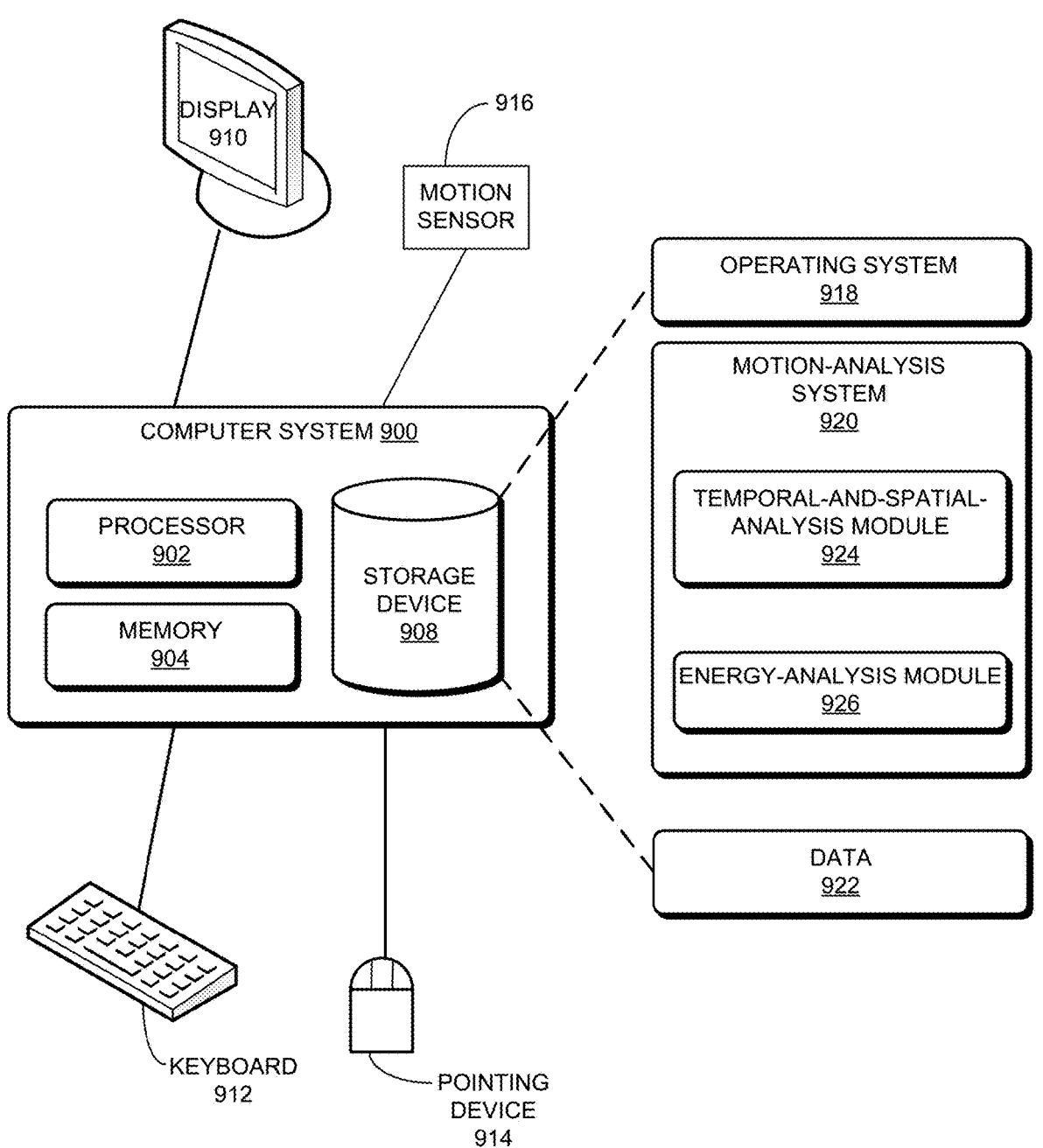
FIG. 9 illustrates an exemplary computer system that facilitates motion analysis, according to one embodiment.

FIG. 9 illustrates an exemplary computer system that facilitates motion analysis, according to one embodiment. In this example, a computer system 900 includes a processor 902, a memory device 904, and a storage device 908. Furthermore, computer system 900 can be coupled to a display device 910, a keyboard 912, a pointing device 914, and a motion sensor 916. Storage device 908 can store codes for an operating system 918, a motion-analysis system 920, and data 922.

Motion-analysis system 920 can include instructions, which when executed by processor 902 can cause computer system 900 to perform methods and/or processes described in this disclosure. Specifically, motion-analysis system 920 can include instructions for implementing a temporal-and-spatial-analysis module 924 and an energy-analysis module 926.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The foregoing descriptions of various embodiments have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention.

What is claimed is:

1. A method for assessing a risk of falling based on gaits of a human user, the method comprising:

attaching a motion sensor to a belt at a location directly behind a lumbosacral joint of the human user;

monitoring, by the motion sensor, a walking or running motion of the human user, wherein monitoring the motion comprises determining a sampling rate of the motion sensor based on a stride frequency of the walking or running motion, obtaining acceleration data associated with the walking or running motion, and applying one or more filters to remove sensor noise and the stride frequency from the acceleration data, and wherein the acceleration data comprises three components corresponding to three spatially orthogonal directions;

for each orthogonal direction of the three spatially orthogonal directions, determining, by a computer, an amount of oscillatory energy included in the walking or running motion in the orthogonal direction based on a corresponding acceleration component, wherein determining the amount of oscillatory energy comprises performing frequency-domain analysis on the acceleration data and removing a fundamental frequency component to remove non-oscillatory energy included in the walking or running motion;

for at least one orthogonal direction of the three spatially orthogonal directions, obtaining an energy fraction factor by computing a ratio between the amount of the oscillatory energy in the at least one orthogonal direction and a total amount of the oscillator energy;

generating one or more gait-analysis results based on the energy fraction factor associated with each orthogonal direction, wherein the gait-analysis results comprise at least a stability factor and a symmetry index associated with the human user's gaits; and configuring a graphic user interface (GUI) to display the gait-analysis results to the human user, wherein the GUI comprises at least a first region for displaying the symmetry index and a second region for displaying the energy fraction factor corresponding to each orthogonal direction, and wherein the energy fraction factor corresponding to a vertical direction indicates the risk of falling associated with the human user.

2. The method of claim 1, wherein the walking or running motion is along a horizontal plane, wherein the three spatially orthogonal directions comprise: a medial lateral (ML) direction, a vertical (VT) direction, and an anterior posterior (AP) direction.

3. The method of claim 1, wherein the gait-analysis results further comprise an efficiency factor.

4. The method of claim 1, wherein performing the frequency-domain analysis comprises:

performing a Fourier transform (FT) on the acceleration data to obtain a plurality of frequency components of the acceleration;

computing, for each frequency of a predetermined set of frequencies, a frequency component of the oscillatory energy at that frequency; and summing the computed frequency components of the oscillatory energy.

5. The method of claim 1, wherein the motion sensor comprises at least one of: a three-axis accelerometer, a gyroscope, and a magnetometer.

6. The method of claim 1, wherein the computer comprises a mobile computing device, and wherein the motion sensor is integrated into the mobile computing device.

7. The method of claim 6, further comprising:

forwarding, by the mobile computing device, output of the motion sensor to a remote server; and receiving, from the remote server, the gait-analysis results.

8. A non-transitory computer-readable storage device storing instructions that when executed by a computer cause the computer to perform a method for assessing a risk of falling based on gaits of a human user, the method comprising:

obtaining acceleration data associated with a walking or running motion of the human user, wherein obtaining the acceleration data comprises determining a sampling rate of the motion sensor based on a stride frequency of the walking or running motion wherein the acceleration data is collected by a motion sensor attached to a belt at a location directly behind a lumbosacral joint of the human user and comprises three components corresponding to three spatially orthogonal directions, and wherein the motion sensor is coupled to the computer via a wired or wireless link;

applying one or more filters to remove sensor noise and the stride frequency from the acceleration data;

for each orthogonal direction of the three spatially orthogonal directions, determining an amount of oscillatory energy included in the walking or running motion in the orthogonal direction based on a corresponding acceleration component, wherein determining the amount of oscillatory energy comprises performing frequency-domain analysis on the acceleration data and removing a fundamental frequency component to remove non-oscillatory energy included in the walking or running motion; and for at least one orthogonal direction of the three spatially orthogonal directions, obtaining an energy fraction factor by computing a ratio between the amount of the oscillatory energy in the at least one orthogonal direction and a total amount of the oscillator energy;

generating one or more gait-analysis results based on the energy fraction factor associated with each orthogonal direction, wherein the gait-analysis results comprise at least a stability factor and a symmetry index associated with the human user's gaits; and configuring a graphic user interface (GUI) to display the gait-analysis results to the human user, wherein the GUI comprises at least a first region for displaying the symmetry index and a second region for displaying the energy fraction factor corresponding to each orthogonal direction, and wherein the energy fraction factor corresponding to a vertical direction indicates the risk of falling associated with the human user.

9. The non-transitory computer-readable storage device of claim 8, wherein the walking or running motion is along a horizontal plane, wherein the three spatially orthogonal directions comprise: a medial lateral (ML) direction, a vertical (VT) direction, and an anterior posterior (AP) direction.

10. The non-transitory computer-readable storage device of claim 8, wherein the gait-analysis results further comprise an efficiency factor.

11. The non-transitory computer-readable storage device of claim 8, wherein performing the frequency-domain analysis comprises:

performing a Fourier transform (FT) on the acceleration data to obtain a plurality of frequency components of the acceleration;

computing, for each frequency of a predetermined set of frequencies, a frequency component of the oscillatory energy at that frequency; and summing the computed frequency components of the oscillatory energy.

12. The non-transitory computer-readable storage device of claim 8, wherein the motion sensor comprises at least one of: a three-axis accelerometer, a gyroscope, and a magnetometer.

* * * * *